United States Patent
Grobler et al.

(10) Patent No.: US 9,585,955 B2
(45) Date of Patent: Mar. 7, 2017

(54) LIPID AND NITROUS OXIDE COMBINATION AS ADJUVANT FOR THE ENHANCEMENT OF THE EFFICACY OF VACCINES

(71) Applicant: North-West University, Potchefstroom (ZA)

(72) Inventors: Anne Frederica Grobler, Potchefstroom (ZA); Abraham Frederik Kotze, Potchefstroom (ZA)

(73) Assignee: North-West University, Potchefstroom (ZA)

( * ) Notice: Subject to any disclaimer, the term of this patent is extended or adjusted under 35 U.S.C. 154(b) by 252 days.

(21) Appl. No.: 14/075,681

(22) Filed: Nov. 8, 2013

(65) Prior Publication Data

US 2014/0178431 A1 Jun. 26, 2014

Related U.S. Application Data

(63) Continuation of application No. 11/794,503, filed as application No. PCT/IB2006/050286 on Jan. 26, 2006, now abandoned.

(30) Foreign Application Priority Data

Jan. 28, 2005 (ZA) .................................. 2005/0856

(51) Int. Cl.
| | |
|---|---|
| *A61K 39/39* | (2006.01) |
| *A61K 39/05* | (2006.01) |
| *A61K 39/205* | (2006.01) |
| *A61K 39/29* | (2006.01) |
| *A61K 39/00* | (2006.01) |

(52) U.S. Cl.
CPC .............. *A61K 39/39* (2013.01); *A61K 39/05* (2013.01); *A61K 39/205* (2013.01); *A61K 39/292* (2013.01); *A61K 2039/55544* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 5,853,752 A | 12/1998 | Unger et al. | |
| 5,942,237 A | 8/1999 | Gizurarson et al. | |
| 6,221,377 B1 | 4/2001 | Meyer | |
| 6,235,282 B1* | 5/2001 | Riviere ................ | A61K 9/0019 424/1.11 |
| 7,033,813 B2* | 4/2006 | Castor .................... | A61K 39/00 435/236 |
| 2002/0012673 A1 | 1/2002 | Schroder | |
| 2009/0010964 A1 | 1/2009 | Grobler et al. | |

FOREIGN PATENT DOCUMENTS

| | | |
|---|---|---|
| GB | 425406 | 3/1935 |
| WO | WO-0047224 | 8/2000 |
| WO | WO-0047225 | 8/2000 |
| WO | WO 02/05849 A2 * | 1/2002 |
| WO | WO-0205849 | 1/2002 |

OTHER PUBLICATIONS

"U.S. Appl. No. 11/794,503, Final Office Action mailed Mar. 8, 2010", 12 pgs.
"U.S. Appl. No. 11/794,503, Non Final Office Action mailed May 10, 2013", 14 pgs.
"U.S. Appl. No. 11/794,503, Non Final Office Action mailed Sep. 11, 2009", 15 pgs.
"U.S. Appl. No. 11/794,503, Preliminary Amendment Jun. 28, 2007", 10 pgs.
"U.S. Appl. No. 11/794,503, Response filed Dec. 8, 2009 to Non Final Office Action mailed Sep. 11, 2009", 10 pgs.
"U.S. Appl. No. 11/794,503, Response filed Feb. 12, 2009 to Restriction Requirement mailed Dec. 11, 2008", 10 pgs.
"U.S. Appl. No. 11/794,503, Response filed Jun. 24, 2009 to Restriction Requirement mailed May 28, 2009", 10 pgs.
"U.S. Appl. No. 11/794,503, Restriction Requirement mailed Dec. 11, 2008", 7 pgs.
"U.S. Appl. No. 11/794,503, Restriction Requirement mailed May 28, 2009", 10 pgs.
"U.S. Appl. No. 11/797,503, Response filed Jul. 8, 2010 to Final Office Action Mar. 8, 2010", 9 pgs.
Schroder, Ulf, et al., "Nasal and parenteral immunizations with diphtheria toxoid using monoglyceride/fatty acid lipid suspensions as adjuvants.", Vaccine, 17(15-16), (Apr. 9, 1999), 2096-103.
"26—Biologicals", Monthly Index of Medical Specialties (MIMS), Times Media of South Africa, (Apr. 2016), pp. 393-403.

* cited by examiner

*Primary Examiner* — Nick Zou
(74) *Attorney, Agent, or Firm* — Schwegman Lundberg & Woessner, P.A.

(57) ABSTRACT

The invention provides for a method of enhancing immunological responses to an antigen in a vaccine formulation, and for a vaccine formulation that provides for an enhanced immunological response to an antigen. In the method and formulation the antigen is administered with an adjuvant which adjuvant comprises a solution of nitrous oxide gas in a pharmaceutically acceptable carrier solvent for the gas and which adjuvant includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil with ethylene oxide.

22 Claims, 4 Drawing Sheets

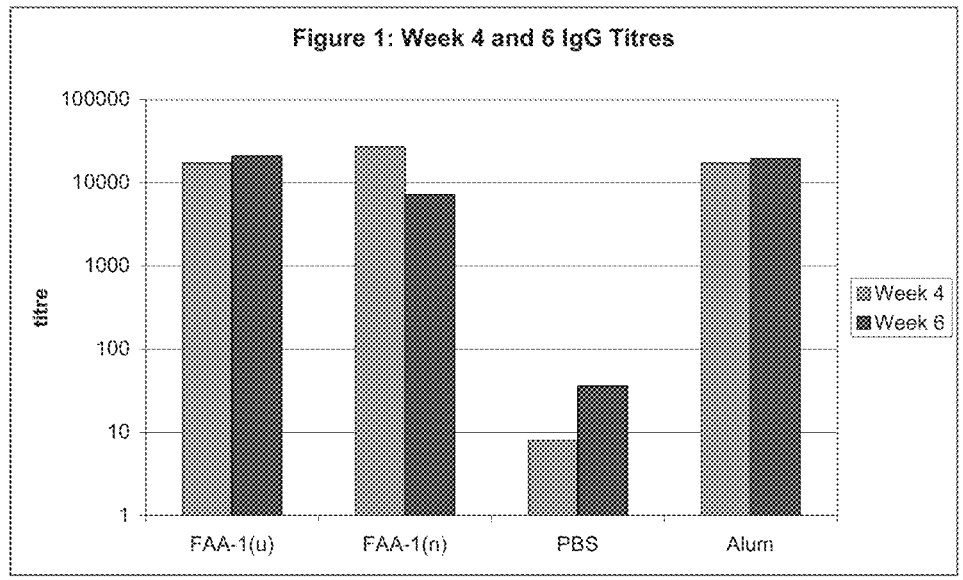
FIGURE 1
FIGURE 2
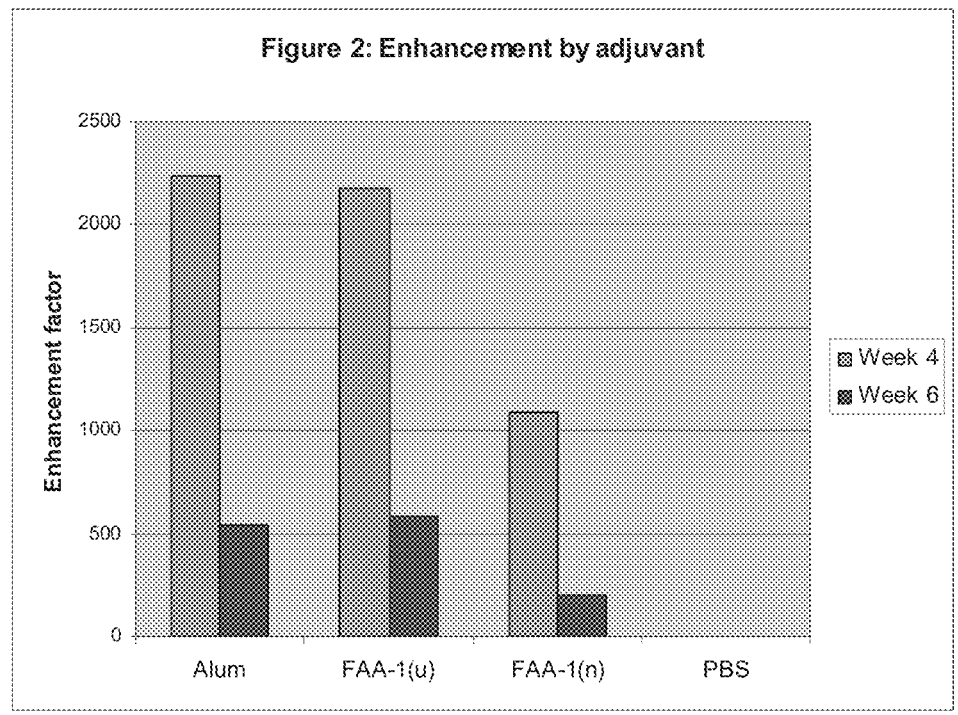

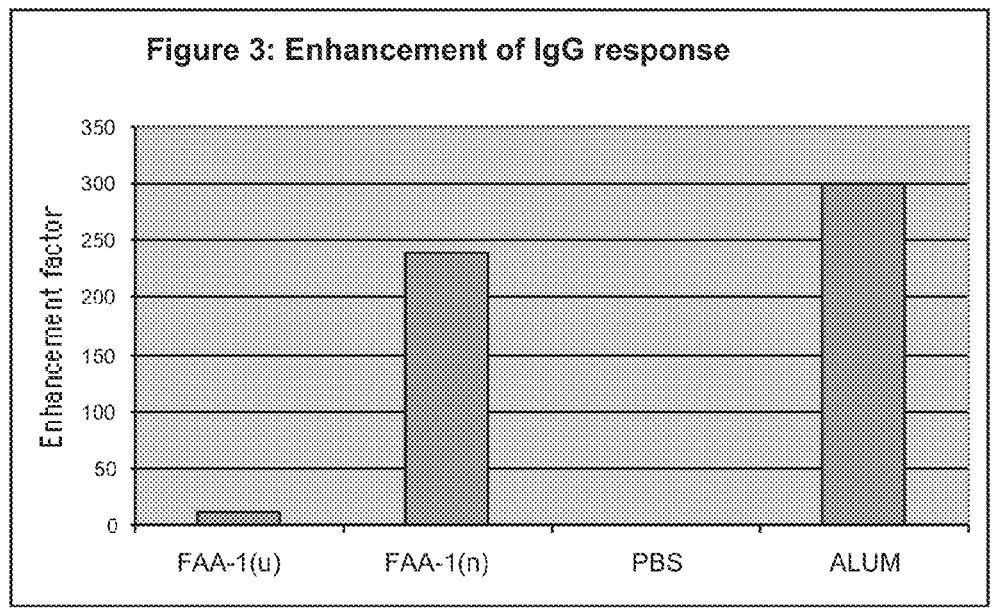
FIGURE 3
FIGURE 4
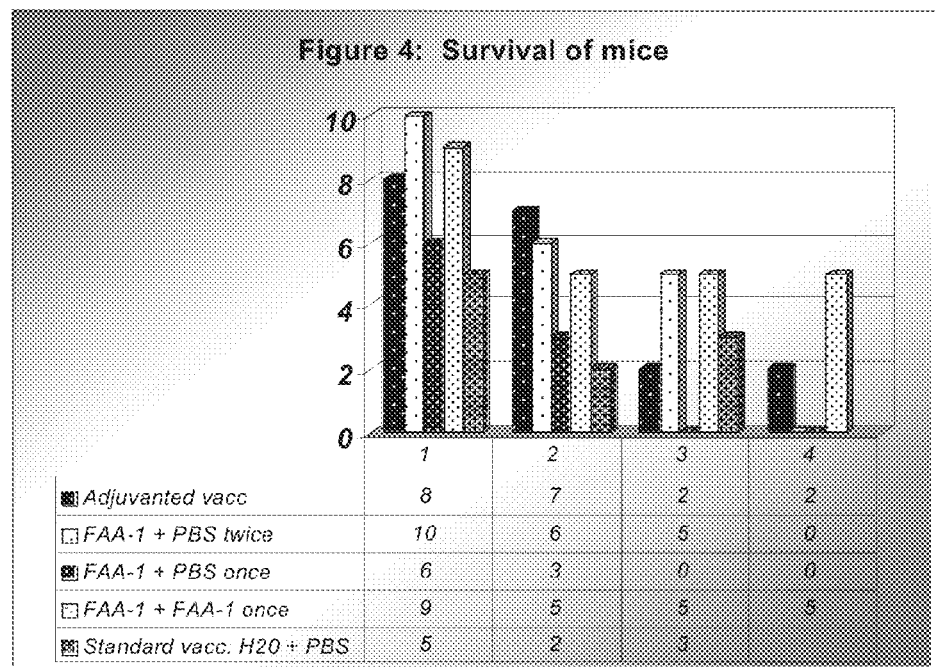

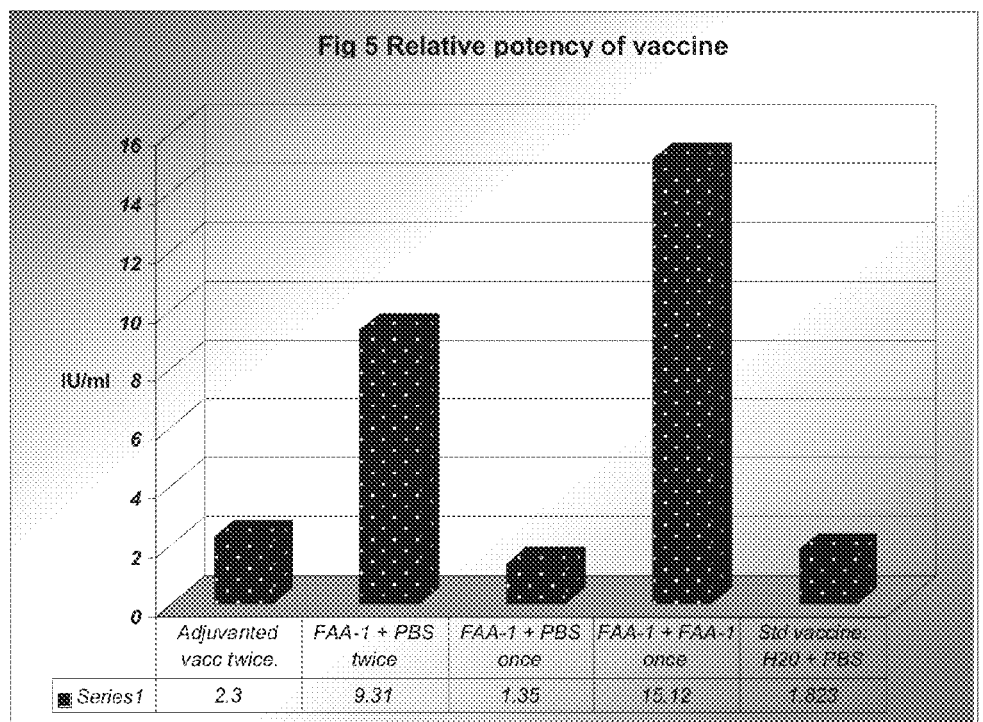
FIGURE 5
FIGURE 6
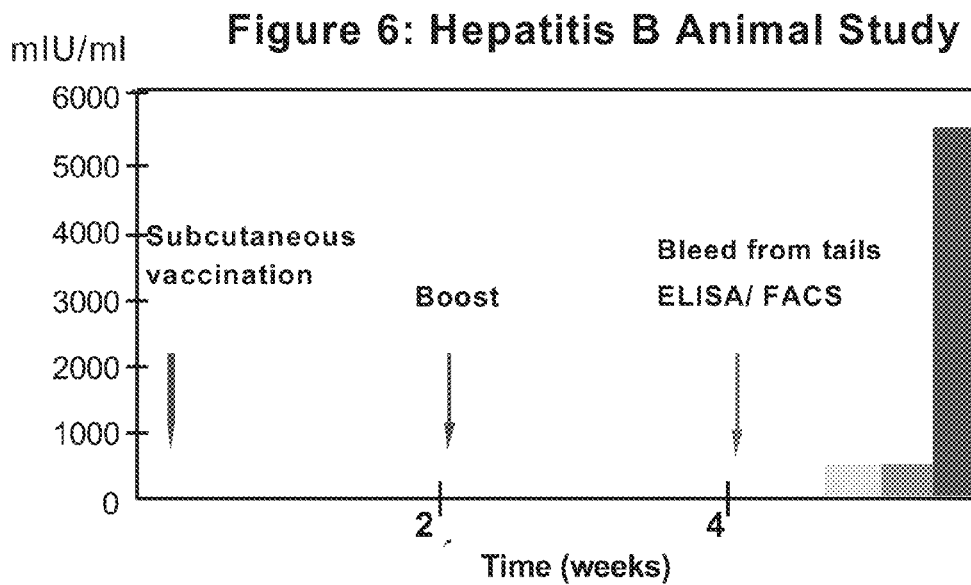

LIPID AND NITROUS OXIDE COMBINATION AS ADJUVANT FOR THE ENHANCEMENT OF THE EFFICACY OF VACCINES

RELATED APPLICATIONS

This application is a nationalization under 35 U.S.C. §371 of PCT/IB2006/050286, filed Jan. 26, 2006 and published as WO 2006/079989 A2, on Aug. 3, 2006, which claimed priority under 35 U.S.C. §119 to South Africa Application No. 2005/0856, filed Jan. 28, 2005; which applications and publications are incorporated herein by reference and made a part hereof.

FIELD OF THE INVENTION

This invention relates to pharmaceutical preparations (which expression is herein intended to include veterinary preparations) for use in the prevention of disease by inoculation against infective organisms afflicting the animal body (which expression is herein intended to include the human body).

BACKGROUND TO THE INVENTION

In EP 93912877.3 and U.S. Pat. No. 5,633,284 and their equivalents there is disclosed that dermatological or topical compositions comprising the combination of nitrous oxide [$N_2O$] and at least one fatty acid, or lower alkyl ester thereof, in a dermatologically acceptable carrier medium, are useful in the treatment of a variety of skin, muscle and joint disorders. It further disclosed therein that such combinations might beneficially also include additional active ingredients. The following active ingredients are specifically mentioned in this regard: coal tar solution, collagen, nicotinamide, nicotinic acid, lanolin, vitamin E, methyl salicylate, arnica and H1-antagonist antihistamines of which only diphenhydramine chloride is specifically mentioned. In WO97/17978 and U.S. Pat. No. 6,221,377 and their corresponding applications and patents there is further disclosed that the action of analgesic, anti-inflammatory and anti-pyretic drugs may be enhanced by administering such drugs in conjunction with a medium which comprises nitrous oxide and at least one long chain fatty acid selected from the group consisting of oleic acid, linoleic acid, alpha-linolenic acid, gamma linolenic acid, arachidonic acid, and any of the $C_1$ to $C_6$ alkyl esters of such long chain fatty acids, mixtures of such acids and mixtures of such esters. The medium may comprise the mixture known as Vitamin F Ethyl Ester and may optionally further comprise eicosapentaenoic acid [$C20:5\omega3$] and decosahexaenoic acid [$C22:6\omega3$].

In WO 02/05850 there is disclosed that the effect of anti-infective drugs may be enhanced by formulation thereof in the same carrier medium.

In WO 02/05851 it is disclosed that the effect of known agents affecting the central and/or peripheral nervous system may similarly be enhanced by their formulation in the same carrier medium.

In WO 02/05849 it is disclosed that the same carrier medium may also beneficially be used for the transportation of nucleic acid compounds across cell membranes.

Antigens for use in forming vaccines are not amongst the active ingredients mentioned in the aforementioned patents and patent applications as being capable of being formulated with beneficial effect with the aid of the carrier medium therein disclosed.

The aforementioned disclosures would not have been understood as suggesting that the nitrous oxide and fatty acid combination have any adjuvant contribution in the preventative effect against diseases caused by infective agents. Within the context of the disclosure in the above-mentioned patent family the notional addressee most likely would, as did the inventor, have understood the role of the anti-infective agents to be the treatment of patients already suffering from an infection.

It has now surprisingly been found that the aforesaid medium and media related thereto may itself act as an adjuvant, thereby enhancing the immunogenicity of known vaccines.

The expression "vaccine" as used herein is intended to have its extended meaning as compound(s) contributing in the prevention of infectious disease by any method or mechanism of priming of the body, and to include viral-based, peptide-based, bacterially-based, VLP-based, and synthetic compound-based formulations, but to exclude anti-infective agents used for the treatment of disease.

The exclusion of anti-infective agents from the ambit of the present invention is introduced without thereby conceding that the aforementioned patents and applications contain any disclosure of any preventative properties of such excluded compounds, or that such properties are obvious in the light of the disclosures in such patents or applications. Such inferences are specifically denied. The exclusion is introduced simply to avoid what is anticipated to be a potential obstacle to the grant of a patent in respect of a part of potential subject matter which part in itself is not considered worth contesting during examination as it might unduly delay the implementation in practice of the significant features of the present invention. It is expected that the remaining bulk of the subject matter of the present invention will greatly contribute to the accessibility of vaccines for the prevention of a large range of infections, at significantly reduced costs in cases such as Hepatitis B.

The expression "therapeutic vaccine" is further intended to cover vaccines which serve to prevent and/or treat an existing infection by eliciting and/or enhancing a specific immune response to the infective agent without the use of antimicrobial, antifungal or antiviral agents. The expression is hence intended to be understood in the wider sense of the immune response, namely all compounds that contribute in eliciting or enhancing an immune response against specific microscopic and sub microscopic organisms. This term is further specifically intended to include all antigens or native and synthetic biologicals falling within class 26 (Biologicals) of the pharmacological classification employed in the Monthly Index of Medical Specialities ("MIMS") published by Times Media in South Africa. It is thus intended to include:

anti-bacterial vaccines;
anti-fungal vaccines;
anti-viral vaccines (including anti-retroviral vaccines);
anti-protozoal agents;
and anti spirochaete vaccines.

The finding of adjuvanticity of the media referred to above is made against the background of the fact that there appears to be no earlier suggestion in the literature to the effect that either nitrous oxide itself or the addition of nitrous oxide to the long chain fatty acids used in the formulation referred to above, has an additional stimulatory effect on the immunogenicity of vaccines.

In recent years, there has been an increasing interest in the development of novel vaccine systems for prophylactic and therapeutic purposes. Formulation strategies and the use of adjuvants that can affect the immune response in both quantitative and qualitative terms have attracted a lot of attention from those familiar with problems in drug delivery. Early efforts were focussed on parenteral vaccines and on the role of controlled release technologies with an emphasis on biodegradable microspheres[1-3].

The primary aim of vaccination is to prevent disease. Historically, vaccination is the only strategy that has ever led to the elimination of a viral disease, namely smallpox. While the biology of most pathogens is less favourable than smallpox to vaccine development, some vaccines do, to varying degrees, protect humans and animals against related pathogens. An indirect relationship has been observed for vaccine immunogenicity and safety. Human immune responses to synthetic and recombinant peptide vaccines administered with standard adjuvants tend to be poor; hence there is an urgent need for effective vaccine adjuvants to enhance the immunogenicity and immunostimulatory properties of vaccines, although even imperfect vaccines could deliver public health and economic benefits and provide further insights for prevention and treatment strategies. While microbicides may usefully extend prevention options and serve as valuable prototypes for vaccine development, it is not clear that these can be delivered sustainably to everyone at risk.

Targeted vaccine campaigns against diseases such as hepatitis B have generally failed to affect disease incidence. To maximise public health and economic benefit, it may be necessary to aim for universal immunisation of children and young animals. This implies the need for an extremely high level of safety, comparable to current widely used vaccines given to children throughout the world. These considerations have favoured the use of vaccines based on relatively small parts of the pathogens.

There is of course, much greater potential in vaccines that are shown to be capable of inducing potentially relevant immune responses than in those that are not. Animal studies and laboratory measurements of human immune responses may be used to provide 'correlates of protection' that speed up further research and development.

Vaccines primarily use a harmless form of a pathogen, or some component of it, to induce a protective immune response involving one or both arms of the immune system: humoral and/or cell-mediated immunity. Humoral immunity is based on antibodies and the B cells that produce them. Antibodies recognise a specific target, usually a sub-part of a protein of the infective organism. 'Neutralising' antibodies play an important role in fighting off infections whereas cytotoxic T cells or CD8+ cells play a major role in cell-mediated immunity. Cytotoxic T cells are able to destroy most pathogen-infected cells, identified by the presence of very small fragments of pathogen proteins that are displayed on the cell surface, bound to cell proteins. Helper T cells (CD4 cells) recognise fragments of pathogens, displayed on the surface of specialised 'antigen presenting cells (APC)'. These produce proteins, which activate B cells and/or cytotoxic T cells. When the immune system is activated by vaccination, memory T cells and sometimes memory B cells are produced. These cells enable a rapid and effective immune response when the pathogen itself is encountered, preventing infection and/or disease.

A major hindrance that has prevented the development of effective mass immunization programs is the inability to induce an appropriate, protective, immune response. For example, for vaccines against intracellular pathogens cell-mediated immunity, as characterized by cytolytic T-lymphocyte activity, is required[4]. Such a response can be extremely difficult to elicit, especially by recombinant, soluble protein subunits. This deficiency is due to the inability of these antigens to access the machinery of the appropriate antigen-processing pathway. Following an improved understanding of the mechanisms underlying such processing, as well as the realization that delivery systems can affect, quantitatively and qualitatively, the resulting immune response, the last decade has witnessed an intense research effort in this field[4-8]. New adjuvant formulations now mostly contain a vehicle that carries antigens to antigen-presenting cells.

Examples of vehicles are generally particulate e.g. emulsions, microparticles, iscoms and liposomes, and microfluidized squalene-in-water emulsions[4-8]. The main function of such delivery systems is to target associated antigens to antigen presenting cells (APC), including macrophages and dendritic cells. A number of adjuvants that are particulates of defined dimensions (<5 micron) have been shown to be effective in enhancing the immunogenicity of weak antigens in animal models. Two novel adjuvants that possess significant potential for the development of new vaccines include an oil-in-water micro-emulsion and polymeric microparticles.

The parenteral route is still the most common route used for the administration of antigens. However, the induction of an efficient local immune reaction is dependent on the presence of air or food born pathogens at the mucosal surfaces, which presence can result in the production of neutralising antibodies. Furthermore, products given by syringe are inherently more expensive than those which can be taken by mouth or—for example—as a nasal spray. The danger of re-use of needles in underdeveloped countries is a compounding factor.

The tissues of the mucosae encounter the majority of antigens that enter the host and infections of the intestine, respiratory tract and urogenital tract are the most common cause of mortality and morbidity in humans[2]. With mucosal vaccination it is possible to stimulate both arms of the immune system and provide both humoral (antibody) and cell-mediated responses (cytotoxic lymphocytes)[1]. Despite the urge for an efficient mucosal vaccine, its introduction is still hindered by the degradation of antigens during transport to and low uptake by the mucosal associated lymphoid tissue (MALT). To circumvent these problems, antigens for mucosal vaccine delivery can be associated to or co-administered with an adjuvant acting simultaneously as efficient delivery system[3,9].

Since each part of the MALT has its own specific barriers, each administration route needs its own vaccine delivery system. Oral vaccination is firstly complicated due to degradation of antigens by both the acidic environment in the stomach and the enzymes in the gut. Moreover, the soluble antigens are not always taken up efficiently by the M-cells of the gut associated lymphoid tissue (GALT). By entrapping the antigen in microparticulate adjuvants, the antigen may be protected against degradation on its way to the mucosal tissue and efficiently targeted to and taken up by the M-cells[10-13].

Nasal vaccination is mainly complicated by the fast clearance of the antigen and the low uptake by the nasal associated lymphoid tissue (NALT). For antigen transport over the nasal epithelial barrier, three different approaches can be followed: co-administration of the antigen with an adjuvant that contributes to the immune response but is at the same time absorbable by the nasal mucosae, co-administration of the antigen with an absorption enhancer, or entrapment into a microparticulate system to stimulate M-cells, which are also present in NALT, to internalise the antigen[14-15].

A number of strategies to produce protective immune responses have in the past been explored. These include:
a) Live attenuated vaccines—a defective pathogen that would be harmless to subjects e.g. nef deleted viruses. These types of vaccines are not safe for use in some cases.
b) Inactivated or 'killed' vaccines. These have still not been fully evaluated for their ability to protect against pathogens. For instance, challenge viruses grown in cells matched to the host and vaccine strains may or may not shed their envelope proteins during inactivation. This type of vaccine is illustrated in the development of a more effective rabies virus.
c) Recombinant sub-unit vaccines—or peptide vaccines—seek to stimulate antibodies to the pathogen by mimicking proteins on its surface (e.g. the proposed Hepatitis B vaccine). Sub-unit vaccines researched to date have been strain-specific and have produced poor antibody responses. Recent research into adjuvants has opened up new areas of envelope vaccine research, with some vaccines capable of inducing neutralising antibodies effective against a range of pathogen strains.
d) Recombinant vectored vaccines—incorporate genes or parts of genes of the pathogen into established vaccines using delivery systems. Delivery systems may include live but harmless viruses, such as the canary pox viruses. Vector vaccines have been shown to produce pathogen-specific cytotoxic T cell responses in subjects. These can be enhanced with DNA vaccine priming.
e) DNA vaccines and replicons—involve genetic sequences injected into subjects to induce the expression of antigens by cells. In the case of replicons, these sequences are wrapped in the outer coat of an unrelated virus.
f) Combination vaccines or 'prime and boost vaccines'. These entail strategies for the combination of two or more different vaccines to broaden or intensify immune responses. Examples include a vector with antigen to prime a T-cell response with a subunit booster to produce antibodies, or delivery of DNA followed by a vector with genes or gene sequences expressing the same gene(s) or gene sequence. It is possible that two different vaccines could be given at the same time, where one acts more rapidly than the other. This would result in a 'prime-boost' effect from a single dose.
g) An important recent development in vaccine design is the use of synthetic genes to maximise their expression in the human cell. This technique has been used in the design of HIV vaccines that enhanced immune responses in animals and at least three vaccines using this technique have now entered early stage clinical trials. It is important to realise that evidence of immune responses in subjects do not necessarily mean that the vaccine prevent infection. Prevention of infection has to be confirmed in animal and human trials. The above stated problems associated with vaccines have led to the investigations associated with the present invention.

The fatty acid/nitrous oxide-based technology comprise of a unique submicron emulsion type formulation within which stable vesicular structures or particles are formed. It was pointed out, inter alia, in WO97/17978 referred to above that nitrous oxide is a natural gas which is also produced synthetically, that it is also known by the trivial name "laughing gas", and that it has been in use for many years as an inhalation anaesthetic and analgesic, particularly in dentistry.

Nitrous oxide is known to be soluble in water and it has been reported that at 20° C. and 2 atm pressure one liter of the gas dissolves in 1.5 liters of water, see The Merck Index 10th Ed. p. 6499.

There appears to be no suggestion in the literature, other than in the patents and patent applications referred to above, that solutions of nitrous oxide might have any effect on man or animals. As far as the present applicant knows, it has also never been suggested that nitrous oxide may be used in conjunction with fatty acids as an adjuvant to enhance the immune response against antigen-specific diseases.

It is known in the pharmaceutical field that antigens can be formulated in so-called lipid-based formulations. None of these lipid-based formulations are used in combination with nitrous oxide, unlike the present invention in which the combination of nitrous oxide and fatty acids and esters thereof forms the basis of the micro-emulsion adjuvant system. As will be shown below, investigation confirmed the essential role of nitrous oxide in the stimulation of the immune response. The combination of nitrous oxide and fatty acids as an adjuvant for vaccines according to the present invention as described herein shows significant differences to that based on the fatty acids only.

OBJECT OF THE INVENTION

It is an object of the present invention to provide an adjuvant with the characteristic of enhancing the action of antigens, and to provide pharmaceutical preparations of such adjuvants in conjunction with antigens which preparations result in a specific enhanced immunological response, such as an increase in specific neutralizing antibodies, compared to the action of known adjuvant formulations containing the same antigens.

STATEMENTS OF THE INVENTION

According to the present invention there is provided a method of enhancing direct or subsequent immunological responses to an antigen in a vaccine formulation, comprising the step of administering the antigen with an adjuvant which adjuvant comprises a solution of nitrous oxide gas in a pharmaceutically acceptable carrier solvent for the gas and which adjuvant includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the $C_1$ to $C_6$ alkyl esters thereof, the glycerol-polyethylene glycol esters thereof and the reaction product of hydrogenated natural oils composed largely of ricinoleic acid based oils, such as castor oil with ethylene oxide.

According to a further aspect of the present invention there is provided a pharmaceutical preparation suitable for use as a vaccine comprising an antigen, which is formulated with an adjuvant which adjuvant comprises a solution of nitrous oxide in a pharmaceutically acceptable carrier solvent for the gas and which includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and the derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil, with ethylene oxide.

The antigen may be selected from the group comprising all possible antigens.

In a preferred form of the invention, the antigens utilised in the method or formulation may comprise any one or more of the different types of antigens as herein defined, namely: peptides, inactivated viruses, inactivated bacteria and virus-like particles (VLPs) or any combination thereof.

The antigen may be any antigen suitable to elicit an immunogenic response against the causative agent of an ailment, or infection by an agent, selected from the group consisting of: *Bacillus* Calmette-Guérin Cholera, *Haemophilus* Type B, Meningococcal, Pertussis, Pneumococcal, Tetanus, Typhoid, Diphtheria, Hepatitis A, Hepatitis B, Influenza, Measles, Mumps, Poliomyelitis, Rabies, Rubella, Tick-borne Encephalitis, Varicella and Yellow Fever.

The invention is thus concerned with the following types of vaccines:

Bacterial Vaccines
    *Bacillus* Calmette-Guérin Vaccine
    Percutaneous *Bacillus* Calmette-Guérin Vaccine
    Cholera Vaccine
    *Haemophilus* Type B Conjugate Vaccine
    Meningococcal Polysaccharide Vaccine
    Pertussis Vaccine
    Pneumococcal Polysaccharide Vaccine
    Tetanus Vaccine
    Typhoid (Strain Ty 21a) Vaccine, Live (Oral)
    Typhoid Polysaccharide Vaccine
    Typhoid Vaccine Bacterial Toxoids
    Diphtheria Vaccine
    Tetanus Vaccine Viral Vaccines
    Hepatitis family of vaccines (inactivated, peptide, VLP)
    Human papilloma virus vaccine (VLP)
    Inactivated Influenza Vaccine (Whole Virion)
    Inactivated Influenza Vaccine (Split Virion)
    Inactivated Influenza Vaccine (Surface Antigen)
    Measles Vaccine, Live
    Mumps Vaccine, Live
    Inactivated Poliomyelitis Vaccine
    Poliomyelitis Vaccine, Live (Oral)
    Rabies Vaccine
    Rubella Vaccine, Live
    Tick-borne Encephalitis Vaccine, Inactivated
    Varicella Vaccine Live
    Yellow Fever Vaccine Mixed Vaccines
    Diphtheria and Tetanus Vaccine
    Diphtheria, Tetanus and Pertussis Vaccine
    Diphtheria, Tetanus and Pertussis (Acellular Component) Vaccine
    Diphtheria, Tetanus and Pertussis (Acellular Component) and *Haemophilus* Type B Conjugate Vaccine
    Diphtheria, Tetanus and Pertussis (Acellular Component) and Diphtheria,
    Tetanus and Pertussis (Acellular Component) and Inactivated Poliomyelitis
    Vaccine
    Hepatitis A (Inactivated) and Hepatitis B (peptide) Vaccine
    Measles, Mumps and Rubella Vaccine, Live It is envisaged that the list will expand as new antigens or different forms of antigens and new combinations are developed.

Depending on the specific antigen, the adjuvant may include the eicosapentaenoic acid [C20: 5ω3] and/or decosahexaenoic acid [C22: 6ω3] or modifications of these as additional long chain fatty acids to at least one of the other components of the carrier medium defined above.

The reaction product of hydrogenated natural oils composed largely of ricinoleic acid based oils with ethylene oxide is preferably produced from castor oil of which the fatty acid content is known to be predominantly composed of ricinoleic acid. The product may be modified as to the extent of hydrogenation, ethylation and the addition of groups such as polyethylene glycol. A range of such products is marketed by BASF under the trade description of Cremophor grades.

The carrier solvent for the nitrous oxide gas may be water or any of the pharmaceutically acceptable alcohols, ethers, oils or polymers such as a polyethylene glycol or the like. The oil may be organic or mineral oil. The organic oil may be an essential oil based on long chain fatty acids having between 14 and 22 carbon atoms in the fatty acid. The oil may also be of either natural or synthetic origin and, if of natural origin, it may be either plant oil or animal oil. As plant oils those rich in gamma linolenic acid [GLA] are preferred and as animal oil dairy cream may be used.

In the preferred form of the invention the solution is an aqueous solution saturated with nitrous oxide. The oil component and aqueous component may be separately packaged and only mixed directly before administration. Preferably the water is deionised and purified to be free of microbes and endotoxins.

When the formulation containing the antigen is to be in a liquid (including an encapsulated liquid) presentation for oral administration or in a nasal or bronchial or pulmonary spray or in the form of an injectable formulation, such formulation may incorporate, as part of the administration medium, water or acceptable other liquid into which the nitrous oxide is dissolved and in which the fatty acid(s) or ester(s) thereof is either dissolved or suspended or emulsified along with the antigen by being formulated therewith. Likewise, where the antigen is to be administered to the patient by being applied as a topical, buccal or vaginal cream, ointment, spray, lotion or as a suppository, the formulation used in making up such cream, ointment, spray, lotion or suppository may incorporate, along with the antigen formulated therewith, a quantity of water or other liquid containing, and preferably saturated with, nitrous oxide, the long chain fatty acid(s) or ester(s) thereof and the antigen formulated therewith, and, further, such additional excipients and carriers as are conventionally used in the pharmaceutical trade in making up such dosage forms.

The carrier solvent for the nitrous oxide gas may thus in an alternative formulation according to the invention be essentially non-aqueous and composed of at least one fatty acid or ester thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], and ricinoleic acid and derivatives thereof selected from the group consisting of the C1 to C6 alkyl esters thereof, the glycerol-polyethylene glycol esters thereof and the reaction product of hydrogenated or unhydrogenated natural oils composed largely of ricinoleic acid based oils with ethylene oxide.

A formulation suited to transdermal application whether as an injectable, ointment, cream or lotion or in the form of a skin patch providing a reservoir for the formulation is also a preferred form of the formulation according to the invention.

The essential fatty acid component of the composition preferably comprises a mixture of esters of the fatty acids listed above. Thus, in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:

<$C_{16}$: 0
$C_{16.0}$: 8.3%
$C_{18.0}$: 3.5%
$C_{18.1}$: 21.7%
$C_{18.2}$: 34.8%
$C_{18.3}$: 28.0%
>$C_{18}$: 1.6%
unknown: 2.1%

It is further preferred to add to the formulation the long chain fatty acids known as eicosapentaenoic acid [C20:5ω3] and decosahexaenoic acid [C22:6ω3]. Such product combinations are available from Croda under the trade name "Incromega".

Microscopical analyses showed that the formulation of the antigen with an adjuvant as herein described gives rise to the formation of microstructures, within which, or attached to which the antigen is contained in a stable form and from which it is delivered at the site of action.

It is a further aspect of the invention that the formulation, may be prepared to be adapted for mucosal administration, and in particular for nasal administration. It will thereby include mucosal immunogenicity.

The invention has not yet been demonstrated by empirical work to be applicable to all antigens. However in respect of such antigens which have already been formulated with the aforementioned adjuvant of the invention, and evaluated by different methods for the anticipated enhancement of immunogenicity and different administration routes, no negative result has as yet been observed despite the biological and chemical diversity of the antigens which have been investigated. The applicant thus confidently expects on the basis of these preliminary observations in respect of products representing a range of classes of such antigens, that the invention will find general application across the entire spectrum of antigens embraced by these terms as herein defined and of which some examples are set out below.

It is part of the applicant's present postulations by which it seeks to find an understanding of the invention and to which it does not wish to be bound at this stage, that while the administration medium of the present invention serves to transport the adjuvanted antigen formulated therewith most efficiently through the human or animal body, that adjuvant also plays an important role in transferring, by an as yet unexplained mechanism, the antigen to the cells of the immune system thereby to cause an effective immune response. It is in this respect that the applicant believes that the present invention will find general application despite the variety in type, mechanism and application of antigens.

Preliminary Hypotheses of Mechanism of Operation

The mechanism by which the enhancement of action of immunogenicity is achieved by the present invention, is currently under investigation. Some observations in this regard have been recorded above. In addition it is recorded that preliminary observations point to some additional possible explanations. The applicant again does not wish to be bound to any of the tentative explanations it may put forward at this time. It is recorded, however, that it would appear that the long chain fatty acids used in the formulation, in conjunction with the nitrous oxide of the preparation according to the invention, or at least some of these components, form, during the manufacturing process of the formulation, small stable vesicles or micro-sponges, hereinafter referred to as "fatty acid-based particles".

BRIEF DESCRIPTION OF THE DRAWINGS

FIG. 1 is a bar graph showing the systemic immune response against DT.

FIG. 2 is a bar graph showing the enhancement of specific antibody production due to the formulation of the DT antigen with adjuvants.

FIG. 3 is a bar graph showing enhancement of IgG response.

FIG. 4 is a bar graph showing the survival of mice treated with adjuvant preparations.

FIG. 5 is a bar graph showing the relative potencies of various vaccine adjuvant combinations.

FIG. 6 is a bar graph showing the comparative efficacy of several FAA based vaccines.

Figure 7:
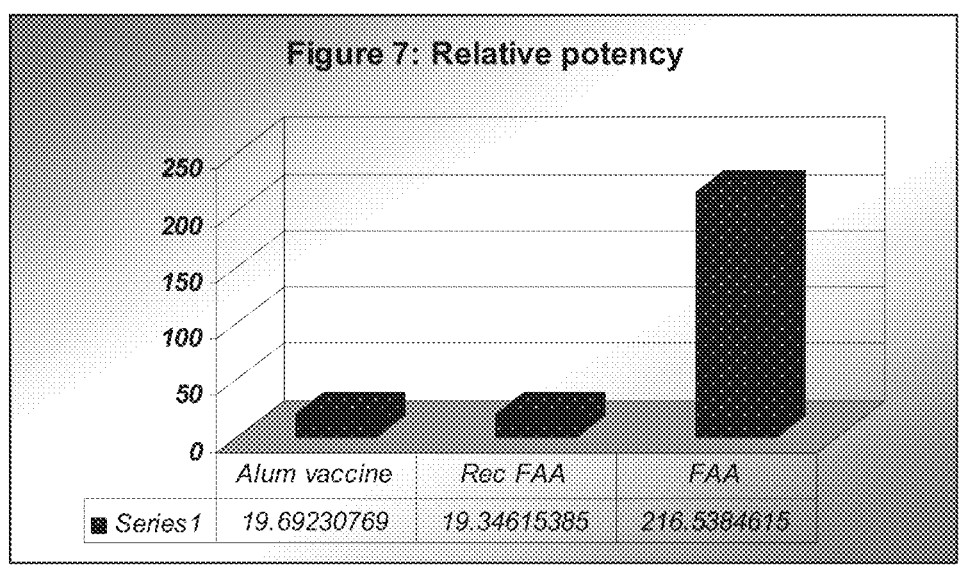
FIG. 7 is a bar graph showing the relative potencies of different vaccines.

1. The Structural Characteristics of the Formulation of the Preparation

Nitrous oxide and the unsaturated long chain fatty acids forming part of the administration medium are formulated by being mixed with designated antigens to form the particles containing the antigen. The particles contain a lipid phase which is adjuvantic in nature, (a) synthetic polymer(s) which is particulate nature, and a gas, nitrous oxide, which seems to activate or potentiate the combination of these particles. Several of the characteristics of the particles contribute to its acting as an effective vaccine adjuvant:

- The entrapment capacity and delivery efficiency of the particles;
- The polyphylic nature of the particles—the particles are well suited to entrap combination of hydrophilic and hydrophobic molecules, such as in the entrapment of antigens and immunostimulatory molecules;
- The passive targeting of the particles and the affinity between particles and lipid structures, such lipid rafts in cell membranes; and
- The particles seem to carry no safety or toxicity danger.

These characteristics as well as the results obtained with some antigens used in conjunction with the particles will be discussed below.

2. The Composition, Number and Size of the Particles

Both the results obtained with the present invention, and literature relating to this field, indicate that different administration routes require differently sized particles for the delivery of an effective vaccine. Furthermore, the type and quantity of antigen loaded into the particles and the absorption capabilities of the particles are to a large extent determined by the composition, number and size of the particles. The sizes of the various types of antigens (compare for instance peptides and viruses) differ dramatically and need to be accommodated. The ability to repeatably manipulate the size and number of the particles is therefore important. The relationship between size and number of particles in this invention seems not to be directly proportional but can be manipulated by the degree of nitrous oxide saturation, which has been shown to have an influence on the size and number of particles formed;

the addition of various polyunsaturated fatty acids;

a change in the ratio of the fatty acids used;

a change in the modification or derivatisation of the fatty acids used;

the addition of biological molecules such as peptides; and the use of various sized synthetic polymers.

Two important observations have been made in this regard:

a) It was found that when the unsaturated long chain fatty acids used are 20 carbons or more, the microstructures formed are spherical with sub-compartments similar to those seen in a sponge.

These structures are stable and it is our belief and observation that antigens (specifically peptides) fit ideally in these sub-compartments so that the antigens are able to bind to specific epitopes or receptors at the target cell surface. When unsaturated long chain fatty acids of 16 to 20 carbons are used, the form of the microstructures are vesicular with a dynamic field of moving auto fluorescent particles surrounding the vesicles.

3. Stability

The particles appear to remain structurally intact after 24 months at room temperature. Any loaded compound remains entrapped during this time. This stability feature is believed to be of substantial significance in the use of vaccines.

4. Absence of Cytotoxicity

The particles, at applicable concentrations, have no apparent cytotoxicity or toxicity, as has been shown in cell culture, animal and human studies.

5. Mechanism of Action 5.1 Loading Efficiency

The high loading efficiency of the particles can be demonstrated by the high degree of entrapment of dipthteria toxoid (DT) and inactivated rabies viruses in particles according to the present invention as were illustrated by Confocal Laser Scanning Microscopy (CLSM). The inactivated viruses were a generous gift from the SA State Vaccine Institute, now the BIOVAC Institute.

5.2 Absorption and Transport

The particles of the invention seem to act as an absorption mechanism in the case of nasal and oral administration and a transport mechanism in the case of parenteral administration to deliver antigens to immune competent cells. The delivery efficiency relates to tissue penetration, cell adsorption, interaction between the components of the cell membrane and the particles, internalisation of particles by cells, and intra-cellular stability.

5.3 Release

The result of high delivery efficiency is the release of antigens not only at membrane sites, but also at intracellular sites, resulting in an enhanced efficacy of said vaccine. The particles act in synergism with the antigen to attain enhanced immunogenicity. The release rate of the particles is influenced by their composition. Prolonged and/or controlled release particles may be used with the aim of combining the prime and boost elements of vaccination.

5.4 Pliability and Elasticity

Confocal laser scanning microscopy (CLSM) shows that the conformation of particles may be changed by their environment. For instance, when the vesicles move through biological barriers, such as circulatory capillaries, the conformation changes in order to accommodate extravascation has been visualised by microscopy.

The unsaturated long chain fatty acid component contributes to cell integrity by its contribution to membrane maintenance. The nitrous oxide component of the particles of the present invention enhances membrane fluidity, which presumably has a positive effect on adsorption, absorption and other membrane bound processes. The composition of the invention has been found to have beneficial effects on the immunogenecity of antigens.

These beneficial effects are believed to be attributable to the dynamic characteristics of the fatty acid-based particles.

5.5. Dynamic Inter-Lipid Vesicle Relationships

It has been shown that particle inter-lipid and particle/cell relationships do exist. The particles can combine to resize themselves continuously without detriment to their stability. These interactive membrane characteristics make the movement of the vesicles through the cells optimal.

Despite the inter-relationships of the particles, it was shown that the particles are stable in blood and body fluids for up to 5 hours.

EXAMPLES OF THE INVENTION

Without thereby limiting the scope of the invention some examples will now be described to illustrate the invention.

Preparation 1

Preparation of FAA-1 for the Parenteral Rabies and Nasal Diphtheria Toxoid (DT)-Vaccines Step 1: The buffer solution applicable to the specific antigen is saturated with nitrous oxide at ambient pressure using a pressure vessel and sparger. In the case of rabies the buffer used was phosphate buffered saline (PBS), in the case of the DT for nasal administration, distilled water was used.

Step 2: The following group of fatty acids was heated to 70° C.: 21% oleic acid, 34% linolenic acid, and 28% linoleic acid. These fatty acids were modified by esterification with an ethylene group of the carboxy terminal. The pegylated, hydrogenated fatty acid, ricinoleic acid (also known by the INCI name as PEG-n-Hydrogenated Castor Oil), was heated to 80° C. and mixed with the first group of fatty acids at 70° C. The ratio of the first group of fatty acids to the latter fatty acid was 3:1.

Step 3: The buffer solution was heated to 70° C. and mixed with the fatty acid mix to a final concentration of 1.85%. This fatty acid mixture constituted the adjuvant and is herein referred to as FAA-1($\mu$). The β-symbol indicates the micro size range of the particles, which were between 2-5 μm in size, as determined by particle size analysis on a Malvern sizer. FAA-1(n) was prepared from FAA-1(µ) by sonication (short term) or by increasing the ricinoleic acid component (long term).

Step 4: Entrapment of the antigen in the adjuvant: The respective antigens were entrapped in the different adjuvant formulations by thorough mixing in a Vibramix for 3 hours (rabies) or 4 hours (DT) at room temperature.

Preparation 2

Preparation of FAA-2 for Parenteral Hepatitis B Vaccine

To the fatty acids contained in FAA-1 above was added
1. dl-α-Tocopherol as anti-oxidant
2. additional ethylated fatty acids DHA (decahexonoic acid) and EPA (eicosapentanoic acid). The preferable amount of the two fatty acids for this invention was 0.2%.
3. Entrapment of the Hepatitis B peptide occurred by mixing for 30 minutes in a Vibramix at ambient temperature.

Stable particles of fairly homogeneous sizes ranging from 20 nm to 50 µm can be manufactured with ease on a large scale. The size and shape of the particles can be reproducibly controlled. The use of FAA-1 and FAA-2 in animal studies as it pertains to this invention is described below. The following antigens considered to be representative and hence demonstrative albeit not exhaustive of the range of vaccines to which the invention relates, were used in the cell and animal studies to confirm the invention:

A toxoid as antigen (diphtheria)
An inactivated virus as antigen (Rabies)
A protein/peptide as antigen (Hep B)

Some examples of the studies and its results are described in the examples below:

Example 1

Determination of the Capacity of an FAA-1/DT Vaccine to Induce a Systemic Immune Response after Oral and Nasal Administration Respectively This example pertains to the enhancement of the immune response to the diphtheria toxoid specifically in a nasally and orally administered vaccine in animals in comparison to the currently used gold standard—an aluminium hydroxide (alum)-based parenteral vaccine.

1. Objective of the Study:

The primary objective of this study was to assess the efficacy of FAA-derived formulations of the present invention in enhancing the systemic immune response after oral and nasal administration of the model antigen DT when compared with antigen administered in a) PBS saline
b) Alum by parenteral route.

Desai et al[16] showed that chitosan particle uptake by M-cells is dependent on the size of the particles as well as the hydrophobic/hydrophilic character of the particles. It has been established that particles with sizes in the nanometer range are more readily taken up by M-cell located in the Peyer's patches. The secondary objective aimed to determine whether a) the size of the FAA particles had any influence on the increase in the immune response for DT and
b) the oral or nasal immune response was comparable to that obtained with the use of alum as adjuvant, using the parenteral administration route.

2. Background to the Study:

The parenteral route is still the most common route to administer antigens. Although the introduction of effective oral or nasal vaccines would improve patient compliance and diminish costs and the need for qualified personnel to administer antigens, most vaccines still have to be administered parenterally. In light of the AIDS epidemic an alternative administration route would be beneficial, especially in developing countries, as is evidenced for instance by recent reports from such developing countries that nurses have injected up to 170 school children with the same needle during immunisation campaigns. Furthermore, mucosal vaccination induces both a local as well as a systemic immune response in contrast to parenteral vaccination that results in the induction of a systemic immune response only. After the induction of an efficient local immune reaction, air or food born pathogens can be neutralized upon arrival at the mucosal surfaces.

The literature reveals that various studies on the design and application of different adjuvants have been tested in the mouse model. The model is therefore well described. Few of the adjuvants tested were found to be comparable to that of the aluminium hydroxide-adjuvanted parenteral vaccines currently in use. For example, the results of Van der Lubben et al.[17] suggested that chitosan microparticles were less efficient in stimulating an immune response after intranasal administration, as only half of the mice nasally vaccinated showed an immune response.

3. General Methodology of Vaccinations:

3.1 Nasal Vaccination in Mice.

The following groups of mice received nasal administrations of the formulations.

I. Positive control 1: 40 Lf DT in PBS nasally administered
II. Positive control 2: 40 Lf DT adsorbed to alum (aluminium hydroxide) administered via subcutaneous injection. (Registered dosage form)
III. FAA-1(μ) with 40 Lf DT
IV. FAA-1(n) with 40 Lf DT
V. Negative control 1: FAA-1 (μ) without DT
VI. Negative control 2: FAA-1 (n) without DT In each of the groups, 10 SPF balb/c female mice, aged 6 weeks, were vaccinated. Balb/c mice have previously been used in oral and nasal vaccination studies with diphtheria toxoid as antigen and results showed that this animal model is suitable for these studies. Half of the mice (5) were sacrificed by decapitation in order obtain blood samples for IgG determination in week 4. The other half was similarly treated in week 6. In each case the DT adsorbed to alum was injected subcutaneously as positive control.

Vaccine Administration:

Nasal formulations were given in a volume of 10 μl/day (5 μl in each nostril). The total dose of DT was distributed over three consecutive days in week 1 and 3.

Sample Collection:

Blood and nasal washes were collected in applicable containers after decapitation. No anticoagulant was present. Serum was prepared by centrifugation. Samples were stored at −20° C.

3.2 Oral Vaccination in Mice.

The following groups of 6 mice each were vaccinated during the study:
- I. Positive control 1: 40 Lf DT in PBS orally administered
- II. Positive control 2: 40 Lf DT adsorbed to alum (aluminium hydroxide) administered via subcutaneous injection. (Registered dosage form)
- III. FAA-1 (µ) with 40 Lf DT
- IV. FAA-1 (n) with 40 Lf DT
- V. Negative control 1: FAA-1 (µ) without DT
- VI. Negative control 2: FAA-1 (n) without DT Vaccine Administration:

Formulations were administered orally by intragastric feeding with a blunt needle. Mice were vaccinated on three consecutive days in week 1 and 3. The dose was divided and the total volume fed was less than 300 µl.

Blood Sampling:

According to the literature, an immune response should still be observable in week 6. Therefore blood was collected as for the nasal study at the end of week 6 for the determination of the IgG titre. Samples were analysed with an antigen-specific Enzyme Linked Immuno Sorbent Assay (ELISA).

4. Design, Calculations and Statistical Evaluation:

i) Experimental design: The experimental design for both the nasal and the oral study was a parallel design where the animals were arranged according to treatment groups and one treatment is administered per experimental animal.

ii) Number of groups of experimental animals: The number of animals is in accordance with previously published studies and was discussed and confirmed with the Department of Statistics of the North-West University, South Africa.

iii) Random assignment of experimental animals in groups: All mice were of approximately the same age and were comparable in physical size. The animals were divided randomly into groups of 10 for the nasal study and 6 for the oral study. The mice were placed into numbered containers. Treatment was randomly assigned to each animal group. The study was not blind, as the same researcher prepared and administered the toxoid, collected the samples and performed the analyses. All administrations and collections were supervised and checked by a qualified researcher. The oral and nasal studies, including the analyses, were performed by two different researchers in order to decrease the chance of any possible bias. Background variables were minimized as far as possible by measures such as using a single batch of mice from the supplier, using the same laboratory equipment for all analyses, and obtaining blood samples and nasal washing on the same day for all mice. The oral and nasal studies each included their own controls (see negative control groups). The animals at the breeding facility are monitored and care is taken that they remain pathogen free.

iv) Statistical methods: Analysis of the samples taken is performed with an Enzyme Linked Immuno Sorbent Assay (ELISA), which is a sensitive and specific assay widely used in the analysis of biological samples. In both the oral and nasal studies, the IgG titers (systemic immune response) obtained with the ELISA assays, were statistically compared to the controls with $p<0.05$. The two treatments were compared to each other by Pearson's.

5. Results:

5.1 Nasal Vaccination

The studies conducted on adjuvant formulation FAA-1, involving the association of the DT antigen prepared as set out in Preparation 1 of the present invention, showed a dramatic enhancement in vaccine efficacy compared to the positive PBS-DT control formulation. The immune responses obtained were comparable with that found for the alum-adjuvanted parenteral administration.

Table 1 reflects the results obtained for one of the serial dilutions of the ELISA assay:

TABLE 1

| Ig G at dilution 1:320 | | | | | | | |
|---|---|---|---|---|---|---|---|
| | Mouse 1 | Mouse 2 | Mouse 3 | Mouse 4 | Mouse 5 | Ave | Stdev |
| Week 4 | | | | | | | |
| FAA-1 (u) | 20480 | 10240 | 10240 | 40960 | 5120 | 17408 | 14299.4 |
| FAA-1 (n) | 20480 | 2560 | | | 20480 | 27136 | 10346.1 |
| PBS | 0 | 40 | 0 | 0 | 0 | 8 | 17.9 |
| Alum | 5120 | 20480 | 20480 | 20480 | 20480 | 17408 | 6869.2 |
| Week 6 | | | | | | | |
| FAA-1 (u) | 2560 | 40960 | 20480 | 20480 | 20480 | 20992 | 13594.5 |
| FAA-1 (n) | 2560 | 2560 | 5120 | 20480 | 5120 | 7168 | 7550.9 |
| PBS | 320 | 80 | 320 | 0 | 0 | 144 | 138.6 |
| Alum | 10240 | 20480 | 20480 | 40960 | 5120 | 19456 | 13738.4 |

As expected, the negative controls showed no antibody response at any time, either locally or systemically. The positive control (PBS saline with antigen) showed a small but observable systemic immune response, as reflected by the determined IgG titre. Unfortunately, two of the mice in the week 4 FAA-1 (n) group died due to the inoculation procedure. The deaths were not related to the specific adjuvant used.

FIG. 1 illustrates the systemic immune response against DT as reflected by the titres of neutralizing antibodies against DT found in the blood after 4 and 6 weeks. The titres are set out on the Y-axis on logarithmic scale.

FIG. 2 illustrates the enhancement of specific antibody production due to the formulation of the DT antigen with the adjuvants. The positive control PBS-DT was used as reference and divider. The enhancement relative to this positive control was >2000 fold for Alum and FAA-1 (μ) and >1000 fold for FAA-1 (n) 4 weeks after the initial inoculation. By week 6, the enhancement in response has decreased to just more than 500 fold in the case of Alum and FAA-1 (μ) and 200 fold in the case of FAA-1 (n). These results confirm that the size of the particles plays a role in the degree of systemic immune response elicited after nasal administration. The covariance between the alum-based and FAA-1 (μ)-based immune response was 676800.7901, whereas that between the alum-based and FAA-1 (n) was 377679. The statistical differences between the PBS-DT control and the three adjuvanted groups were less than 0.05 in each case.

5.2 Oral Vaccination

The results of the oral vaccination indicates that the immune responses observed are much lower than in the case of the nasal vaccination, but the enhancement is nevertheless statistically significant in the case of Alum and FAA-1 (n), as shown in FIG. 3 below:

The results confirm the importance of the size of the adjuvant particles: in contrast to the nasal administration, the systemic immune response was enhanced 40-fold by the nano-sized particles of the present invention, but only 2-fold by the micro-sized particles. The enhancement of the specific antibody was lower after oral administration than after nasal vaccination, presumably for some of the following reasons: the enhancement is determined relative to the positive PBS-DT control, which was 2.9 higher in the oral study, and the diphtheria toxoid is sensitive to low pH, to which it was exposed in the stomach. However, the response of the Alum-based vaccine is also significantly lower than after nasal administration and was parenterally administered and thus not exposed to factors such as low pH. These two studies therefore indicate that nasal vaccination results in a better immune response than oral vaccination for this particular toxoid. Nevertheless, vaccination with both alum-based and FAA-1 (n)-based toxoid led to a statistically significant response (>10 AU/ml) which complies with the international requirements of the World Health Organization for vaccine efficacy of diphtheria (A level>0.01 AU/ml is protective in man according to the WHO).

6. Conclusions

The FAA was administered by the nasal and the oral route as solution, which contained either micro- or nano-particles within which the toxoid were entrapped. No response was observed for unloaded FAA-1 (μ) or FAA-1 (n) in either the oral or nasal study. After vaccination with the positive control, PBS-DT, the immune response was low and did not comply with the set requirements. In addition, only two of the 5 mice in the nasal and 1 of the 6 mice in the oral study showed some immune response after vaccination with PBS-DT.

The role played by adjuvants in enhancing the efficacy of a vaccine is clearly illustrated by these studies. The alum-based parenteral vaccination resulted in a significant systemic immune response, similar to that described in the literature. Similarly, both the FAA-1 (μ) and FAA1-(n) showed comparable and statistically significant systemic immune responses after nasal administration, whereas FAA-1 (n), but not FAA-1 (μ), showed a comparable and statistically significant immune response after oral administration.

The results of these studies suggest that the present invention should enable the use of the nasal administration route for vaccination instead of the parenteral route, doing away with the need for needles and injectables. The invention will therefore contribute to safer, cheaper and environmentally friendlier vaccines.

Example 2

Determination of the Enhancement of Efficacy of an FAA-1 Based Rabies Vaccine Compared to that of a Commercial Vaccine The animal studies in EXAMPLE 1 showed that the fatty acid-based adjuvant FAA-1 described in this invention is effective in enhancing the specific immune response systemically (IgG antibodies) against diphtheria after nasal and oral administration. All mice vaccinated with DT associated to FAA-1 micro- or nano-particles produced enough neutralising antibodies to be protected against the effects of diphtheria toxin.

This example pertains to the enhancement of the immune response to inactivated rabies viruses for the formulation of a rabies vaccine with a higher efficacy than that of the currently used commercially available parenteral vaccine. The efficient delivery of the rabies antigen by parenteral administration was investigated in animal studies, using the rabies vaccine formulation shown above. Mice was injected either intraperitoneally or subcutaneously with inactivated rabies virus (control), or FAA-associated inactivated virus, challenged and their survival measured.

1. Study Objectives:

The primary objective of these investigations was the determination of efficacy of the present invention as parenteral adjuvant. Example 1 described above did not address the efficacy of the fatty acid-based adjuvant for parenteral administration. These studies pertain to a direct comparison of the adjuvanticity of the adjuvant according to this invention and the commercially used adjuvant alum.

The secondary objectives of the study included:
Example 1 described a model system with a model antigen. In this example, the antigen investigated is that used in the industry for the preparation of commercial vaccines.
One of the objectives was to expand the number of animals per study and to confirm the repeatability of the observed enhancement in efficacy in animals.
To determine whether the number of dosages can be reduced in the described invention.
To determine whether the fatty acid-based adjuvant itself contributes to the immune response.

2. Background to the Study

Rabies is an acute, progressive, incurable viral encephalitis that affects both humans and animals[1-3]. The causative agents are neurotropic RNA viruses in the family Rhabdoviridae, genus *Lyssavirus* that use carnivores as well as bat species as hosts. Viral transmission occurs mainly via animal bite, and once the virus is deposited in peripheral wounds, centripetal passage occurs towards the central nervous system. After viral replication, there is centrifugal spread to major exit portals, the salivary glands, creating a channel for the infection of the next host[1-3].

Despite continued attempts at medical intervention, rabies retains the dubious distinction of being the infectious disease with the highest case-fatality ratio[3]. At least 50 000 people die from rabies annually, more than 10 million receive post-exposure vaccination against this disease, whilst more than 2.5 billion people live in regions where rabies is endemic[4]. These figures are an underestimation, as some of the endemic regions are not easily accessible, causing under-reporting. Rudimentary surveillance indicates that one person dies from the disease every 15 minutes, and more than 300 others are exposed. Infection of humans from rabid animals is almost invariably fatal once symptoms of disease occur. Although incubation periods average 1-3 months, disease occurrence days or years after exposure has been documented. Children aged 5-15 years are at particular risk.

Rabies is found on all continents except Antarctica. More than 99% of all human deaths from rabies occur in Asia, Africa and South America; India alone reports 30 000 deaths annually. From a global perspective, given the widespread distribution, public-health concerns, veterinary implications, and economic burdens, rabies is the most important viral zoonosis[5]. The WHO encourages carefully designed studies on the feasibility and impact of incorporating modern rabies vaccines in the early immunization programmes of infants and children in communities where rabies is a major health problem.

The most efficient and cost-effective method of control is vaccination. Historically, many rabies vaccines were derived from infected brain tissue. Although relatively cheap, they are of varying levels of efficacy. The potency and safety of rabies vaccines have greatly improved in the past 20 years with the development of cell-culture propagation. Nonetheless, in some countries the only available vaccine is of nerve-tissue origin from sheep, goats, or suckling rodents.

The WHO has endorsed the complete discontinuation of unpurified neural tissue vaccines in developing countries by 2006, to be replaced with cell-culture vaccines. The only way this will be possible is for countries to have access to an inexpensive high quality cell culture vaccine. A standard cell-culture vaccination regimen (e.g. the Essen schedule) consists of a vaccine on days 0, 3, 7, 14, and 28 administered in the deltoid or in the anterior thigh for children. A typical intradermal regimen (8-0-4-0-1-1) consists of vaccine administered at eight sites on day 0, followed by four intradermal inoculations on day 7, and vaccine at one site on days 28 and 90.

Vaccines used for intradermal postexposure prophylaxis have included human-diploid-cell vaccine, Vero-cell rabies vaccine, purified chicken-embryo-cell vaccine, and purified duck-embryo-cell vaccine. After Aventis Pasteur, the South African Biovac Institute (BI) is the second laboratory in the world to have adapted a rabies virus to grow in human diploid cell (HDC). The HDC vaccine is considered to be the "gold standard[6]. It produces high serological titres in patients and contains no foreign animal tissue thus giving rise to fewer adverse effects, but is expensive to produce. HDC vaccines with a higher efficacy will reduce the cost. HDC rabies vaccines are weak antigens and their potency may be enhanced by use of adjuvants[7]. Most human rabies vaccines are not formulated with adjuvant although RVA (Rabies Vaccine Adsorbed onto aluminium phosphate) is available in the USA. However, a recent study in animals comparing the effect of aluminium adjuvant-containing and non-aluminium adjuvant-containing rabies vaccines showed no advantage to having adjuvant present[8]. Nevertheless, use of appropriate adjuvants may be the best way of increasing the potency of HDC rabies vaccines as is commonly used for other inactivated viral vaccines'. In preliminary studies, the fatty acid based adjuvant herewith described resulted in dramatically enhanced levels of protection (9-fold increase in antibody titre compared to unadjuvanted rabies vaccine) against rabies in mice, using the HDC antigen.

3. General Methodology

Various comparative in vitro and animal studies were undertaken on different formulations of the inactivated rabies virus. The rabies vaccine potency was determined by use of challenge experiments in mice (NIH test[9]), rather than in vitro tests based on antigen content[10] as in vitro assays are not able to detect the decrease in potency of rabies vaccines partially degraded by heat[11]. Potency evaluation of inactivated rabies vaccines has been the subject of much investigation; the most widely used is the NIH potency test which gives variable results but is the only test currently accepted by the WHO[12]. This animal test takes 30 days to perform and involves immunisation of mice with test and reference antigens followed by intracerebral challenge with a standard strain of rabies vaccine. Rabies viruses were cultured in lung fibroblasts and then inactivated by the SA State Vaccine Institute according to novel procedures developed by Dr Woolf Katz. The procedure for the culturing of the virus does not form part of the present invention.

Generally, inactivated rabies viruses, mice were injected either intraperitoneally or subcutaneously with each of the two vaccines. A third group of mice, injected with phosphate buffer, were used as control. Six dilutions (up to 1:2500 dilution) of each of the vaccines were administered to 10 mice each (60 mice in total for each vaccine) on day 1, and the inoculation was repeated on day 15. After another 14 days, mice were challenged by intracerebral injection of the live rabies virus. Mice with no resistance or weak immune response against the virus died within a couple of days. A typical animal study is described below:

3.1 Preparation of the Samples:

Serial dilutions of 1/20, 1/100, 1/500 and 1/2500 of the vaccine were used in most studies to determine the potency of the vaccine. The potency of the vaccine is directly proportionate to the number of mice protected against death at each of the serial dilutions. The results of three studies led to the design of the study described below. This animal study contained the following groups of mice:

I. Positive control 1: Standard Vaccine: Two (2) vials standard vaccine are reconstituted in water (provided with the vaccine) and diluted in PBS with the above dilution series to be administered twice as per standard mice vaccination procedure.

II. Test vaccine 1: FAA-1 diluted in PBS: 2 vials standard vaccine are reconstituted in FAA-1 and diluted in PBS with the above dilution series to be injected twice as per standard mice vaccination procedure.

III. Test vaccine 2: FAA-1 diluted in PBS: 2 vials standard vaccine are reconstituted in FAA-1 and diluted in PBS with the above dilution series to be injected once as per standard mice vaccination procedure.

IV. Test vaccine 3: 2 vials of standard vaccine are reconstituted in FAA-1 and diluted in FAA-1 with the above dilution series to be injected once as per standard mice vaccination procedure.

V. Positive control 2: Alum-adjuvanted vaccine with high efficacy provided to BIOVAC Institute diluted according to the above dilution series to be injected twice as per standard mice vaccination procedure.

VI-VIII: Negative control groups receiving no vaccination.

3.2 Vaccine Administration and Challenge:

The mice were divided into groups of 10 mice per cage. Each group received one of the dilutions of one of the vaccine preparations as per the standard described rabies vaccine testing procedure of the NIH and the vaccine administration schedule set out in table 2. Three groups of mice received no vaccine preparation and were used as negative control and for the titration of the challenge virus (CVS) on Day 14. A total of 180 balb/c mice were used in this study: all groups contained 4 subgroups each for the 4 serial dilutions, for each of which 10 balb/c mice were vaccinated and challenged, thus 32 mice per group.

TABLE 2

Administration and challenge schedule:

| Group | Injection Day 0 | Injection Day 7 | Challenge Day 14 |
|---|---|---|---|
| I | 0.5 ml i.p. | 0.5 ml i.p | CVS |
| II | 0.5 ml i.p | 0.5 ml i.p | CVS |
| III | 0.5 ml i.p | No injection | CVS |
| IV | 0.5 ml i.p | No injection | CVS |
| V | 0.5 ml i.p | 0.5 ml i.p | CVS |
| VI-VIII | No injection | No injection | CVS Titration |

The administrations of the different vaccines were followed by an intracerebral challenge with live virus after two weeks with applicable dilutions of live infective virus CVS in all of the mice, according to the NIH test.

4. Results

Measurement of the relative potencies of the adjuvant preparations using the NIH test (BI) is determined by survival of the mice. FIG. 4 below illustrates the survival of mice for the four different serial dilutions of each group.

The relative potencies determined for the groups are expressed as IU/ml according to the recommendations of the WHO and are reflected in FIG. 5. Unvaccinated mice and those with a poor immune response died within 6 days (the small bar indicates the group, not the survival of an animal); most of the mice that were inoculated with the current aluminium-based vaccine died, whereas only two of the mice that received the lowest dilution (1:2500) of FAA-based vaccine died. All experiments were performed according to the specifications of the WHO. (WHO. Rabies: Human Vaccines, (2004)
[Web:]
http://www.who.int/rabies/vaccines/human vaccines/en
[Date of use: 27 Jan. 2004]).

The WHO requires a relative potency of 2.5 IU/ml for a rabies vaccine.

5. Conclusion

Rabies vaccination presents with three major problems: the repeated dosage (5×), the parenteral administration and most of all the development of a cell-cultured high efficacy vaccine. The fatty acid-based adjuvant described herewith provides an adjuvant with a significantly increased immunogenic index, using cell-culture prepared antigen.

The results of previous studies and those represented here illustrate that:
  a) of the tested vaccines containing the HDC antigen, only those containing the fatty acid adjuvant described in the present invention answered to the standards set by the WHO;
  b) the higher immunogenic index of the vaccine may facilitate fewer inoculations as illustrated by the mice of Group IV, that received FAA-1 based antigen, diluted with FAA-1 only once, and still resulted in the highest survival and protection of the mice. Decreasing the number of inoculations should limit the cost and increase user-friendliness.
  c) the FAA based vaccine is thus far more effective than the available vaccine and shows inherent immunostimulatory activity and seem to act as booster despite the absence of antigen, once the animal was primed by the first inoculation of FAA-1 and antigen.
  d) The FAA-based vaccine answers to the international requirements for this specific vaccine in terms of efficacy and safety. The FAA-based vaccine is on average 7 to 9 times more effective than the aluminium hydroxide based vaccine.
  e) This study was repeatable and was validated in terms of the study itself, and the statistical significance of the results. The efficient delivery of antigens by parenteral administration was confirmed by similar animal studies, using the rabies vaccine formulation.
  f) The role of the FAA itself in the enhancement of efficacy of the rabies vaccine was determined by a comparing the efficacy of FAA-based rabies vaccine diluted with physiological buffer and the efficacy of FAA-based vaccine diluted with FAA. The results show that dilution with FAA enhances the efficacy of the vaccine dramatically, again illustrating that the FAA-adjuvant has inherent immune-stimulating properties.
  g) The role of nitrous oxide was illustrated by the freeze-drying and reconstitution study—under the vacuum used for freeze-drying, all nitrous oxide are removed. Reconstitution of the FAA-vaccine results in a vaccine in which no nitrous oxide is present. The results indicate that the efficacy of this vaccine is similar to that of the alum-adjuvanted vaccine, but not nearly as effective as the FAA-based vaccines containing nitrous oxide.
  h) The possibility that the enhancement of vaccine efficacy was due to pyrogens contained in the FAA-base formulation, was similarly excluded by the fact that freeze-dried FAA-based reconstituted rabies vaccine shows no such enhancement. The reconstituted vaccine would still contain the pyrogens but the change in FAA structure due to the lyophilization process resulted in loss of vaccine efficacy.

Similar animal studies with various different arms were repeated 4 times. The formulated adjuvant contains components that have been recognized as pharmaceutically safe. There is thus an opportunity to use this human diploid cell (HDC) culture antigen or other antigens in concert with the adjuvant to develop a high quality, low-cost, immunologically effective rabies vaccine. Using this adjuvant, administration of the vaccine may also be expanded to other administration routes, eliminating the use of the parenteral route altogether.

Example 3

Proposed Hepatitis B Vaccine

An estimated 400 million people are chronically infected with the hepatitis B virus (HBV)[13]. Hepatitis B virus (HBV) infection is caused by a small enveloped DNA virus that infects the liver, causing immune mediated hepatocellular necrosis and inflammation. The infection can be either acute or chronic. Clinical severity may range from (a) asymptomatic and completely resolving to (b) symptomatic with progressive and even fatal illness or (c) occasional fulminant hepatic failure. The course of the infection appears to be determined by the host's immune response. In most immunocompetent adults, acute infection leads to an acute hepatitis followed by rapid clearance of the virus and the development of lifelong immunity. If, however, the infection occurs in the neonatal period or in the first years of life, infection with HBV usually becomes persistent. Chronic viral hepatitis infection causes serious health hazards such as liver cirrhosis and hepatocellular carcinoma[14]. Preventive vaccines should allow for the generation of neutralizing antibodies which effectively prevent infection in immunocompetent individuals. The current invention was used in an animal study to ascertain the applicability of the FAA-based adjuvant in enhancing the efficacy of hepatitis B vaccines.

A surface antigen (peptide) of hepatitis B was entrapped in FAA and the efficacy was measured by assaying the specific antibody response obtained after inoculation with PBS with peptide (control), the currently used alum-based vaccine and the FAA-based vaccine. Two weeks after inoculation, the mice (10 animals/group) received a second inoculation. Blood was obtained from the tails of the animals two weeks later, and the number of antibodies determined. The antibodies obtained from FAA-based Hepatitis B inoculated mice were diluted 1:1 to enable measurement. FIG. 6 below illustrates the comparative efficacy of the proposed FAA-based vaccine against hepatitis B in mice. FIG. 7 shows the relative potency of the different vaccines, using the results obtained with the peptide antigen alone as divider. Rec FAA is the freeze-dried and reconstituted FAA-based hepatitis vaccine.

The results thus show that entrapment of the peptide antigen in FAA led to an enhancement of Hepatitis B antibody production of more than 10 times that for observed for the alum-based vaccines and 250 times that of the antigen without any adjuvant. As in the case of the proposed rabies vaccine, reconstructed or reconstituted FAA showed a similar response as the alum-based vaccine with no dramatic enhancement.

Many variations of the invention may be devised without thereby departing from the spirit of the invention.

REFERENCES

1. WHO. Rabies: Epidemiology, (2004) [Web:] http://www.who.int/rabies/epidemiology/en/[Date of use: 27 Jan. 2004]
2. O'Hagan, D. T. Drug Targets Infect Disord, 1 (2001) 273-86.
3. Rupprecht, C E, Hanlon, A, and Hemachudha, T. The Lancet; Infectious Diseases, 2 (2002) 101-9.
4. Singh J, Jain D C, Bhatia R, et al. Indian Pediatr 38 (2001) 1354-60.
5. Meltzer M I, Rupprecht C E. Pharmacoeconomics 14 (1998) 365-83.
6. Dreesen D W. Vaccine 15 (Suppl) (1997) S2-S6.
7. Moingeon P, Haensler J, Lindberg A. Vaccine 19 (2001) 4363-4372.
8. Lin H and Perrin P. Zhonghua Shi Yan He Lin Chuang Bing Du Xue Za Zhi 13 (1999) 133-5.
9. WHO Technical Report Series 658, Annex 2, Requirements for rabies vaccine for human use. WHO, Geneva, 1981.
10. Hulskotte E G J, Dings M E M, Norley S G and Osterhause A D M E. Vaccine 15 (1997) 1839-1845.
11. Madhusudana S N, Shamsundarb R and Seetharamanc S. Int. J. Infect. Dis. 8 (2004) 21-25.
12. Brarth R, Diderrich G and Weinmann E. NIH test, a problematic method for testing potency of inactivated rabies vaccine. Vaccine, 1988, 6: 369-377.
13. Vaccines and Biologicals. WHO vaccine-preventable diseases: monitoring system; 2002 global summary
14. Tiollais, P., Pourcel, C. and Dejean, A., The hepatitis B virus. *Nature* 1985. 317, pp. 489-495.

What is claimed is:

1. A method of enhancing direct or subsequent immunological responses to a vaccine containing an antigen, comprising the step of administering a composition of the vaccine combined with an adjuvant, wherein the antigen of the vaccine is not inactivated by nitrous oxide, and wherein the adjuvant comprises a solution of nitrous oxide gas in a pharmaceutically acceptable carrier solvent selected from the group consisting of water, one or more of a pharmaceutically acceptable alcohol, ether, oil or polymer including polyethylene glycol and which adjuvant further comprises at least one fatty acid or a suitable derivative thereof selected from the group consisting of oleic acid, linoleic acid, alpha-linolenic acid, gamma-linolenic acid, arachidonic acid, eicosapentaenoic acid [C20: 5w3], decosahexaenoic acid [C22: 6w3], ricinoleic acid and derivatives thereof selected from the group consisting of the C1 to C6 alkylesters thereof, the glycerol-polyethylene glycol esters thereof and a reaction product of hydrogenated natural oils comprising ricinoleic acid based oils.

2. A pharmaceutical preparation comprising a composition of an adjuvant combined with a vaccine containing an antigen, wherein the antigen is not inactivated by nitrous oxide and, wherein the adjuvant comprises a solution of nitrous oxide in a pharmaceutically acceptable carrier solvent selected from the group consisting of water and one or more of a pharmaceutically acceptable alcohol, ether, oil or polymer including polyethylene glycol and which adjuvant further comprises at least one fatty acid or a derivative thereof selected from the group consisting of oleic acid, linoleic acid, alpha-linolenic acid, gamma-linolenic acid, arachidonic acid, eicosapentaenoic acid [C20: 5w3], decosahexaenoic acid [C22: 6w3], ricinoleic acid and derivatives thereof selected from the group consisting of C1 to C6 alkyl esters thereof, glycerol-polyethylene glycol esters thereof and reaction products of hydrogenated natural oils comprising ricinoleic acid based oils.

3. The method of claim 1 in which the antigen of the vaccine utilized in the method is selected from the group consisting of antigenic peptides, inactivated viruses, inactivated bacteria and virus-like particles (VLPs).

4. The method of claim 1 wherein the antigen of the vaccine is suitable to elicit an immunogenic response against the causative agent of an ailment, or infection by an agent, selected from the group consisting of: *Bacillus* Calmette-Guerin Cholera, *Haemophilus* Type B, Meningococcal, Pertussis, Pneumococcal, Tetanus, Typhoid, Diphtheria, Hepatitis A, Hepatitis B, Humanpapilloma virus, Influenza, Measles, Mumps, Poliomyelitis, Rabies, Rubella, Tick-borne Encephalitis, Varicella and Yellow Fever.

5. The method of claim 1 wherein the reaction product of hydrogenated natural oils comprising ricinoleic acid based oils with ethylene oxide is produced from castor oil of which the fatty acid content is known to be predominantly composed of ricinoleic acid.

6. The method of claim 1 wherein the solution is an aqueous solution saturated with nitrous oxide, the water being deionised and purified to be free of microbes and endotoxins.

7. The method of claim 1 wherein the composition is in a liquid presentation for oral administration or in a nasal or bronchial or pulmonary spray formulation or in the form of an injectable formulation, and wherein the composition incorporates the solvent, into which the nitrous oxide is dissolved and in which the fatty acid(s) or ester(s) thereof is either dissolved or suspended or emulsified along with the antigen by being formulated therewith.

8. The method of claim 1 wherein the composition is for administration to the patient as a topical, buccal, nasal or vaginal cream, ointment, spray, lotion or as a suppository, and the composition incorporates the solvent containing, and preferably saturated with, nitrous oxide and, the long chain fatty acid(s) or ester(s) thereof, and, additional optional excipients and carriers.

9. The preparation of claim 2 wherein the composition is made up to be suited to transdermal application as an injectable, ointment, cream or lotion or is in the form of a skin patch providing a reservoir for the composition.

10. The method of claim 1 wherein the fatty acid component of the composition is constituted by the complex known as Vitamin F Ethyl Ester.

11. The method of claim 1 wherein the composition is prepared to be adapted for mucosal administration and in particular nasal administration.

12. A preparation as claimed in claim 2 wherein the composition includes one or more vaccines that render the composition suitable for use to vaccinate against an infectious agent, the vaccine being selected from the group consisting of *Bacillus* Calmette-Guérin Vaccine, Cholera Vaccine, *Haemophilus* Type B Conjugate Vaccine, Meningococcal Polysaccharide Vaccine, Pertussis Vaccine, Pneumococcal Polysaccharide Vaccine, Tetanus Vaccine, Typhoid Vaccine, Diphtheria Vaccine, Tetanus Vaccine, Inactivated Hepatitis A Vaccine, Hepatitis B Vaccine (peptide), Inactivated Influenza Vaccine (Whole Virion), Inactivated Influenza Vaccine (Split Virion), Inactivated Influenza Vaccine (Surface Antigen), Measles Vaccine, Live_Mumps Vaccine, Poliomyelitis Vaccine, Live (Oral)_Rabies Vaccine, Rubella Vaccine, Live_Tick-borne Encephalitis Vaccine, Inactivated Varicella Vaccine, Live Yellow Fever Vaccine, Diphtheria and Tetanus Vaccine, Diphtheria, Tetanus and Pertussis Vaccine, Diphtheria, Tetanus and Pertussis (Acellular Component)_Vaccine, Diphtheria, Tetanus and Pertussis (Acellular Component)_and *Haemophilus* Type B Conjugate Vaccine, Diphtheria, Tetanus and Pertussis (Acellular Component)_and Hepatitis B (peptide) Vaccine, Diphtheria, Tetanus and Pertussis (Acellular Component)_and Inactivated Poliomyelitis Vaccine, Hepatitis A (Inactivated) and Hepatitis B (rDNA) Vaccine, and Measles, Mumps and Rubella Vaccine, Live.

13. The preparation of claim 2 in which the vaccine or vaccines_utilized in the formulation is or are selected from the group consisting of antigenic peptides, inactivated viruses, inactivated bacteria and virus-like particles (VLPs).

14. The preparation of claim 2 wherein the vaccine is suitable to elicit an immunogenic response against the causative agent of an ailment, or infection by an agent, selected from the group consisting of Tuberculosis, Cholera, *Haemophilus* Type B, Meningococcal, Pertussis, Pneumococcal, Tetanus, Typhoid, Diphtheria, Hepatitis A, Hepatitis B, Human_ apilloma virus, Influenza, Measles, Mumps, Poliomyelitis, Rabies, Rubella, Tick-borne Encephalitis, Varicella and Yellow Fever.

15. The preparation of claim 2 wherein the reaction product of hydrogenated natural oils comprising ricinoleic acid based oils with ethylene oxide is produced from castor oil of which the fatty acid content is predominantly composed of ricinoleic acid.

16. The preparation of claim 2 wherein the solution is an aqueous solution saturated with nitrous oxide, the water being deionized and purified to be free of microbes and endotoxins.

17. The preparation of claim 2 which is in a liquid formulation for oral administration or in a nasal or bronchial or pulmonary spray formulation or in an injectable formulation, and wherein the composition incorporates the solvent into which the nitrous oxide is dissolved and the fatty acid(s) or ester(s) thereof which is either dissolved or suspended or emulsified.

18. The preparation of claim 2 formulated to be administered to the patient by topical, buccal, nasal or vaginal cream, ointment, spray, lotion or as a suppository, and wherein such preparation incorporates the solvent containing, and preferably saturated with, nitrous oxide, the long chain fatty acid(s) or ester(s) thereof and additional optional excipients and carriers.

19. The preparation of claim 2 wherein the reaction product is castor oil with ethylene oxide.

20. The method of claim 1 wherein the reaction product is castor oil with ethylene oxide.

21. The preparation of claim 2 wherein the fatty acid component of the composition is constituted by the complex known as Vitamin F Ethyl Ester.

22. The preparation of claim 2 adapted for mucosal administration and in particular nasal administration.

\* \* \* \* \*

UNITED STATES PATENT AND TRADEMARK OFFICE
CERTIFICATE OF CORRECTION

PATENT NO.         : 9,585,955 B2
APPLICATION NO.    : 14/075681
DATED              : March 7, 2017
INVENTOR(S)        : Grobler et al.

It is certified that error appears in the above-identified patent and that said Letters Patent is hereby corrected as shown below:

On the Title Page

In item (54), in "Title", in Column 1, Line 1-2, before "ADJUVANT", delete "LIPID AND NITROUS OXIDE COMBINATION AS"

In Column 2, under "Other Publications", Line 19, delete "11/797,503," and insert --11/794,503,-- therefor In item (57), in "Abstract", in Column 2, Line 12, delete "[C20:" and insert --[$C_{20}$:-- therefor In item (57), in "Abstract", in Column 2, Line 12, delete "[C22:" and insert --[$C_{22}$:-- therefor In item (57), in "Abstract", in Column 2, Line 14, delete "C1 to C6" and insert --$C_1$ to $C_6$-- therefor In the Drawings On sheet 1 of 4, Fig. 1, delete "FAA-1 (u)" and insert --FAA-1 (μ)-- therefor On sheet 1 of 4, Fig. 2, delete "FAA-1 (u)" and insert --FAA-1 (μ)-- therefor On sheet 2 of 4, Fig. 3, delete "FAA-1 (u)" and insert --FAA-1 (μ)-- therefor In the Specification In Column 1, Line 1-2, before "ADJUVANT", delete "LIPID AND NITROUS OXIDE COMBINATION AS"

In Column 1, Line 51, delete "[C20:" and insert --[$C_{20}$:-- therefor

In Column 1, Line 52, delete "[C22:" and insert --[$C_{22}$:-- therefor

Signed and Sealed this
First Day of May, 2018

Andrei Iancu
*Director of the United States Patent and Trademark Office*

In Column 6, Line 51, delete "[C20:" and insert --[$C_{20}$:-- therefor

In Column 6, Line 51, delete "[C22:" and insert --[$C_{22}$:-- therefor

In Column 6, Line 66, delete "[C20:" and insert --[$C_{20}$:-- therefor

In Column 6, Line 66, delete "[C22:" and insert --[$C_{22}$:-- therefor

In Column 7, Line 1, delete "C1 to C6" and insert --$C_1$ to $C_6$-- therefor

In Column 8, Line 9, delete "[C20:" and insert --[$C_{20}$:-- therefor

In Column 8, Line 10, delete "[C22:" and insert --[$C_{22}$:-- therefor

In Column 8, Line 63, delete "[C20:" and insert --[$C_{20}$:-- therefor

In Column 8, Line 64, delete "[C22:" and insert --[$C_{22}$:-- therefor

In Column 8, Line 66, delete "C1 to C6" and insert --$C_1$ to $C_6$-- therefor

In Column 9, Line 29, delete "[C20:" and insert --[$C_{20}$:-- therefor

In Column 9, Line 30, delete "[C22:" and insert --[$C_{22}$:-- therefor

In Column 12, Line 60, delete "70° C." and insert --70 °C.-- therefor

In Column 12, Line 65, delete "β-symbol" and insert --μ-symbol-- therefor

In Column 13, Line 25, delete "20 nm" and insert --20 μm-- therefor

In Column 14, Line 67, delete "-20° C." and insert -- -20 °C.-- therefor

In Column 16, Table 1, Line 14-15, delete "FAA-1 (u)" and insert --FAA-1 (μ)-- therefor In Column 16, Table 1, Line 21-22, delete "FAA-1 (u)" and insert --FAA-1 (μ)-- therefor In Column 17, Line 33, delete "FAA1-(n)" and insert --FAA-1 (n)-- therefor In Column 19, Line 35, delete "vaccines'." and insert --vaccines[7].-- therefor In the Claims In Column 23, Line 53, in Claim 1, delete "[C20: 5w3]," and insert --[$C_{20}$: 5ω3],-- therefor In Column 23, Line 54, in Claim 1, delete "[C22: 6w3]," and insert --[$C_{22}$: 6ω3],-- therefor

CERTIFICATE OF CORRECTION (continued)
U.S. Pat. No. 9,585,955 B2

In Column 23, Line 55, in Claim 1, delete "C1 to C6" and insert --$C_1$ to $C_6$-- therefor In Column 24, Line 3, in Claim 2, delete "[C20: 5w3]," and insert --[$C_{20}$: 5ω3],-- therefor In Column 24, Line 4, in Claim 2, delete "[C22: 6w3]," and insert --[$C_{22}$: 6ω3],-- therefor In Column 24, Line 5, in Claim 2, delete "C1 to C6" and insert --$C_1$ to $C_6$-- therefor In Column 25, Line 4, in Claim 12, delete "Live Yellow" and insert --Live_Yellow-- therefor In Column 25, Line 26, in Claim 14, delete "Human_ apilloma" and insert --Human_papilloma-- therefor